United States Patent
Barone et al.

(10) Patent No.: US 6,479,040 B1
(45) Date of Patent: Nov. 12, 2002

(54) COSMETIC FORMULATION

(75) Inventors: Salvatore Barone, Staten Island, NY (US); Antonietta Corrigan, Somerville, NJ (US); Mita Mody, Clifton, NJ (US); Melizza Bautista, Dumont, NJ (US); Ralph Macchio, Sparta, NJ (US); Louis Veltry, Milford, PA (US)

(73) Assignee: Coty Inc., New York, NY (US)

( * ) Notice: Subject to any disclaimer, the term of this patent is extended or adjusted under 35 U.S.C. 154(b) by 0 days.

(21) Appl. No.: 09/777,611

(22) Filed: Feb. 6, 2001

(51) Int. Cl.⁷ .......................... A61K 7/00; A61K 7/025; A61K 7/035; A61K 9/14; A61K 31/715
(52) U.S. Cl. .................. 424/64; 424/401; 424/489; 424/502; 424/63; 424/78.03; 424/DIG. 5; 514/2; 514/724; 514/770; 514/783; 514/847; 514/944; 514/952; 514/963; 514/965
(58) Field of Search .................. 424/64, 401, 489, 424/502, 63, 78.03, DIG. 5; 514/2, 724, 770, 783, 847, 944, 952, 963, 965

(56) References Cited

U.S. PATENT DOCUMENTS 5,165,915 A * 11/1992 Tokubo et al.
6,045,783 A    4/2000 Macchio et al. .............. 424/64

* cited by examiner

*Primary Examiner*—Frederick Krass
*Assistant Examiner*—Clinton Ostrup
(74) *Attorney, Agent, or Firm*—Schwegman, Lundberg, Woessner & Kluth, P.A.

(57) ABSTRACT

The present invention includes a cosmetic formulation. The cosmetic formulation comprises a plurality of spheres having a first desiccated volume and having a second hydrated volume. The hydrated volume is greater than the desiccated volume.

22 Claims, No Drawings

COSMETIC FORMULATION

BACKGROUND OF THE INVENTION

The present invention relates to a cosmetic formulation and in particular, to a lipstick formulation.

Cosmetics that color lips are, perhaps, the most widely used and coveted cosmetics that have ever been invented. Women who typically do not wear cosmetics, wear lipstick. This has been the case throughout history. Women have been coloring their lips since at least the time of ancient Egypt. From the ancient Egyptians, through Roman times, then through the period of the Tuscans during the time of the Renaissance, and the French aristocracy, women painted their lips.

The Guerlain company produced one of the first commercially successful lipstick products in about 1880. This lipstick product was a pomade comprising grapefruit mixed with butter and wax. Subsequent lipstick formulations, made by other vendors, included ingredients that damaged the lips. In the early 1900's, a beauty writer cautioned that "the texture of the lips is very sensitive and can hardly stand painting, and the formulations destined to redden the lips only succeed in making the skin hard and wrinkled, and robbing it of all delicacy and pliancy."

After World War I, lipstick formulations included dried and crushed insect bodies, that imparted color to the lipstick, as well as beeswax and olive oil. The olive oil went rancid several hours after application. Despite these shortcomings, by 1924, it was estimated that 50 million American women used lipstick. During the 1920's, a tube of lipstick cost a dime. Lipstick sold at this time was sold in a sliding tube. The first American lipstick in a sliding tube was designed about 1915 by Maurice Levy.

These early lipstick formulations were not indelible. From about the 1920's to the 1990's, lipstick technology was directed to developing indelible, long lasting formulations, new colors, as well as new methods of packaging and applying lipstick. The Krog et al. U.S. Pat. No. 6,045,782, which issued Apr. 4, 2000, describes an anhydrous cosmetic stick for improved transfer resistance. The stick composition included up to 70% of a volatile solvent and up to 40% of a polymeric organosiloxane emulsifier. The emulsifier contained at least one hydrophilic radical and at least one lipophilic radical. Other lip products were also developed over this period. These other products included lip liner, which was used to line lips in an attempt to make them appear larger.

During World War II, lipstick was introduced for use on the battlefield. This lipstick included a sunscreen. Since about the 1990's, lipstick formulations have been considered not only in the context of imparting beauty to a user but also in terms of providing a protection against disease or in augmenting a healthy, youthful appearance. The Lukas et al. patent which issued Aug. 9, 1988, describes a lipstick formulation that includes an antiherpetically active combination of at least one sulphated polysaccharide or sulphatized polymer and a polyethylene glycol mixture.

SUMMARY OF THE INVENTION

One embodiment of the present invention includes a cosmetic formulation. The cosmetic formulation comprises a plurality of spheres. The spheres have a first desiccated volume and a second hydrated volume. The hydrated volume is greater than the desiccated volume.

One other embodiment of the present invention includes a lipstick. The lipstick comprises a plurality of spheres. The spheres have a first desiccated volume and a second hydrated volume. The hydrated volume is greater than the desiccated volume. For some embodiments, the lipstick is substantially free of moisturizers.

Another embodiment of the present invention includes a method for moisturizing lips. The method includes providing a lipstick comprising a plurality of spheres. The spheres have a first desiccated volume and a second hydrated volume. The hydrated volume is greater than the desiccated volume. The method also includes applying the lipstick to lips so that the spheres, having a desiccated volume, are trapped in wrinkles in the lips. The trapped, desiccated spheres take up transdermal water, and thereby become hydrated. The water is retained in the trapped spheres. The hydrated spheres hydrate a user's lips for a time period of at least about 24 hours after color from the lipstick has faded.

Another embodiment of the present invention includes a method for decreasing wrinkles in lips and for increasing lip fullness. The method includes providing a lipstick comprising a plurality of spheres. The spheres have a first desiccated volume and a second hydrated volume. The hydrated volume is greater than the desiccated volume. The method also includes applying the lipstick to lips so that the lipstick penetrates wrinkles and so that the spheres are hydrated by water in the lips thereby increasing the volume of the spheres and increasing lip fullness.

One other embodiment includes a method for making a lipstick. The method includes providing a plurality of spheres that have a desiccated volume and a hydrated volume. The hydrated volume is over 100 times greater than the desiccated volume. The method also includes suspending the plurality of spheres in an oil or a silicone. The method further includes adding coloring agents to the plurality of spheres in an oil.

Another embodiment includes a lipstick formulation. The lipstick comprises a phase comprising a wax, an alcohol, and lanolin. The lipstick also comprises a phase comprising castor oil and a phase comprising castor oil and a plurality of spheres. The spheres have a first desiccated volume and a second hydrated volume. The hydrated volume is at least about one-hundred times greater than the desiccated volume. The lipstick also includes phases comprising mica and a fragrance.

One other embodiment of the present invention includes one other lipstick formulation. The lipstick formulation comprises a wax, a triglyceride, a polydecene, an oil and a plurality of spheres. The plurality of spheres have a desiccated volume and a hydrated volume. The hydrated volume is at least about 100 times greater than the desiccated volume. The lipstick formulation also includes a coloring agent and an antioxidant.

DETAILED DESCRIPTION

In one method aspect, the present invention includes a method for increasing moisture in lips for a period of time up to at least about 24 hours after application of a lipstick. In particular, the method of the present invention increases moisture in lips for hours after the lipstick applied to lips has worn away. The method includes providing a lipstick comprising a plurality of spheres. The spheres comprise polyglyceryl dioleate, diethylene glycol monoethyl ether, vegetable oil polyethylene glycol esters, propylene glycol monolaurate, silyl sililic anhydride and wheat powder, pentaerythrityl, tetraisostearate, silica dimethyl silylate, and acacia senegal.

For some embodiments, the lipstick formulation is substantially free of moisturizers, such as guanidine, glycolic acid, glycolate salts such as ammonium and quaternary alkyl ammonium, lactic acid and lactate salts, aloe vera in any of its variety of forms, polyhydroxy alcohols such as sorbitol, glycerol, hexanetriol, propylene glycol, butylene glycol, hexylene glycol, polyethylene glycols, sugars and starches, sugar and starch derivatives, hyaluronic acid, lactamide monoethanolamine, acetamide monoethanolamine and mixtures thereof. The lipstick is applied to lips. Even though the lipstick is substantially free of conventional moisturizers, the user's lips are moisturized by the lipstick and remain moisturized for at least up to about 24 hours after application of the lipstick.

What is believed to occur is that the spheres in the lipstick formulation penetrate interstices formed by lip tissue. The term "interstices" as used herein refers to wrinkles or crevices within the lips. Once the spheres penetrate the interstices, the spheres become trapped. The spheres become hydrated within the interstices. In particular, the spheres absorb transdermal water as the water migrates to the skin surface. The spheres retain the migrating water and prevent the water from evaporating. Instead, the spheres retain the water and moisturize the user's lips for many hours after the lipstick has been applied and has worn off a user's lips.

In one product aspect, the cosmetic formulation of the present invention comprises a plurality of spheres comprising polyglyceryl dioleate, diethylene glycol monoethyl ether, vegetable oil polyethylene glycol esters, propylene glycol monolaurate, silyl sililic anhydride and wheat powder, pentaerythrityl, tetraisostearate, silica dimethyl silylate, and acacia senegal. The spheres impart a smoothing effect and decrease wrinkles when applied to skin. The spheres, when in a desiccated state, have a mean diameter of about 20 microns.

The spheres swell when changing from a dehydrated to a hydrated state. To enhance sphere rehydration, a high molecular weight biopolymer, which is known for its moisturizing and filmogenous characteristics, is encapsulated in the spheres. After penetrating the epidermis, the spheres rehydrate by trapping trans-epidermal water loss. This rehydration adds volume to the skin and smooths away surface imperfections. When applied to lips in a lipstick, the spheres are positioned within wrinkles in the lips. When the spheres hydrate, they expand to a volume several hundred times greater than their desiccated volume of about 20 microns. When the spheres expand, they "fill in" the wrinkles in lips and increase lip fullness. The term "lip fullness" as used herein refers to a lessening of wrinkles that results when the spheres expand and push the lip topography outward, imparting an appearance of lip fullness.

The methods and products of the present invention surprisingly demonstrate that lips can be moisturized by a topical formulation that is substantially free of materials conventionally known to be moisturizers. Furthermore, the methods and products of the present invention surprisingly demonstrate that lip moisturizing occurs for hours after lipstick has not only been applied, but long after the lipstick color has worn off a user's lips.

The spheres are made from cross-linked vegetal proteins. The vegetal proteins are derived from wheat germ. The wheat germ protein has a high molecular weight, over 100,000 Daltons, and confers filmogenic and hydrating properties to a cosmetic formulation. The basic amino acids in wheat germ, arginine and lysine, complement the basic amino acids in keratin, in the skin or hair. The wheat protein binds covalently with keratin chains by disulfide bridges between the sulphated amino-acids of the wheat protein and those of the keratin.

The spheres have a dry matter content of about 70 to 90% and a viscosity of 100 to 5000 cps. The spheres are present in cosmetic formulations in concentrations that range from about 0.01 to 1.5% by weight. The spheres are added to the oil phase of a cosmetic formulation with intense mechanical stirring.

The spheres have a sufficiently small diameter to penetrate the interstices in the horny layer of the skin. The dehydrated spheres swell and fill a volume several hundreds of times greater than their original size. The spheres have a viscosity of 100 to 5000 cps.

The spheres comprise a hydrophobic gel that comprises polyglyceryl-6 dioleate, ethoxydiglycol, apricot kernel oil PEG-6 esters, propylene glycol laurate, silica dimethyl silylate. The wheat protein component is a hydrolyzed wheat protein. The protein includes phenoxyethanol, methylparaben, ethylparaben, propylparaben, and butylparaben. The spheres also include a butylene glycol component.

The spheres are added and are held in an anhydrous preparation, such as an oily gel. The spheres act as sponges in the epidermis structure. The spheres trap water that is usually evaporated. The spheres increase the hydration of the epidermis layers. In one embodiment, the spheres are manufactured by COLETICA of Lyon, France.

The spheres are blended with other ingredients to make a cosmetic. In one embodiment, the spheres are blended with ingredients to make a lipstick. The ingredients include waxes, in a concentration of about 1 to 30 percent. Waxes are solid or semi-solid and are natural or synthetic. The melting point of the wax is about 30 to 120 degrees Centigrade. The wax is derived from animals, plants, minerals, silicone waxes, and petroleum. The waxes include bayberry, beeswax, polyethylene, candelilla, carnauba, ceresin, cetyl esters, hydrogenated jojoba oil and wax, hydrogenated microcrystalline wax, mink wax, montan acid wax, montan wax, ouricury wax, ozokerite, paraffin, PEG-6 beeswax, rice bran wax, synthetic carnauba wax, synthetic japan wax, synthetic wax, polyethylene, stearoxy dimethicone, dimethicone behenate, stearyl dimethicone, and the like.

A lipstick formulation additionally includes a nonvolatile oil. The nonvolatile oil is present in a concentration of about 1 to 20% by weight of the formulation. The oils include essential oils, esters, glyceryl esters of fatty acids, fatty acids, alcohols, and so on. Acceptable esters include acetyl trialkyl citrates, acetylated glycol stearate, cetearyl derivatives, cetyl acetate, cetyl acetyl ricinoleate, cetyl isononanoate, cetyl lactate, cetyl myristate, cetyl octanoate, cetyl oleate, cetyl palmitate, cetyl stearate, hexyl laurate, glycol stearate, glycol palmitate, isostearyl isostearate, jojoba oil, jojoba esters, isostearyl neopentanoate, isostearyl lactate, lauryl acetate, lauryl stearate, myreth derivatives, polyethylene glycol ester derivatives, sucrose derivatives, and so forth.

High molecular weight oils are also usable. These oils include castor oil, lanolin, lanolin derivatives, triisocetyl citrate, caprylic /capric triglycerides, coconut oil, corn oil, cottonseed oil, hydrogenated castor oil, linseed oil, mink oil, palm oil, olive oil, illipe butter, rapeseed oil, soybean oil, sunflower seed oil, tallow, tricaprin, trihydroxystearin, tristearin, trilaurin, trilinolein, trimyristin, triolein, tripalmitin, tristearin, tribehenin, walnut oil, wheat germ oil, cholesterol and so on.

Nonvolatile, nonfluorinated silicones are also acceptable. These silicones include amodimethicone, dimethicone, dimethicone copolyol, dimethiconol, hexadecyl methicone, methicone, phenyl trimethicone, simethicone, dimethylhydrogensiloxane, stearoxy dimethicone, vinyl dimethicone and so on. Fluorinated oils such as fluorinated silicones, perfluoropolyethers, and fluorguerbet citrate esters are also usable.

Emollients and softeners are also added to the formulation. The emollients include isoeicosane, dimethicone, myristyl myristate and behenyl erucate. The emollients are present in a concentration of about 1–60 weight percent.

Other adjutants are also possible ingredients in the formulation of the present invention. The adjutants include alcohols, polyols, stearic acid, magnesium stearate, cetearyl octanoate, corn starch and organic light stabilizers. Oil soluble UVB filters are also included. The filters act as light stabilizers. The filters include 4-aminobenzoic acid derivatives like 4-(dimethylamino)-benzoic acid-(2-ethylhexyl) ester, esters of cinnamic acid such as 4-methoxycinnamic acid-(2-ethylhexyl)ester, benzophenone derivatives like 2-hydroxy-4-methoxybenzophenone; 3-benzylidene camphor derivatives like 3-benzylidene camphor.

Powders are also an ingredient for some lipstick embodiments. The powders are added to impart color to the lipstick. The powders comprise about 5 to 50% of the formulation. The powders include bismuth oxychloride, titanated mica, fumed silica, spherical silica, polymethylmethacrylate, micronized TEFLON, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc roninate, alumina, attapulgite, calcium carbonate, calcium silicate, dextran, kaolin, nylon, silica silylate, silk powder, nylon spheres, ceramic spheres, synthetic polymer powders, powdered natural organic compounds such as ground solid algaes, encapsulated and unencapsulated grain starches, or mixtures of these materials. The particles in these powders may be treated with lecithin, amino acids, mineral oil, silicone oil, or other agents used alone or in combination with these ingredients.

The powder particles also include organic and inorganic pigments. Organic pigments include aromatic dyes such as azo, indigo, triphenylmethane, anthraquinone, and xanthine dyes which are designated as D&C and FD&C blues, browns, greens, oranges, reds, yellows and so forth. Organic pigments include insoluble metallic salts of certified color additives, Lakes. Inorganic pigments include iron oxides, ultramarines, chromium, chromium hydroxide colors and mixtures of these materials. The weight ratio of pigmented to non-pigmented powder particles ranges form 1:20 to 20:1.

Powders which are soluble in water are usable as carriers for the spheres. Soluble powder materials include gums, proteins, protein hydrolysates, and starches. A hydrocolloid such as xanthan, maltodextrin, galactomanan or tragacanth is also included for blending with the spheres.

A fragrance may also be added to the formulation for some embodiments. The fragrance may be volatile or inert. The fragrance comprises one or more of an aldehyde, ketone, ester, alcohol, terpenes, and so forth. A scented oil may have a light floral fragrance such as rose extract, violet extract, or a fruity fragrance such as lime, lemon, orange, geraniol, geranyl acetate, eugenol, isoeugenol, linalool, linalyl acetate, phenethyl alcohol, methyl ethyl ketone, methylionone, isobornyl acetate and so forth. An ingredient such as menthol and its derivatives may also be added to impart a feeling of freshness to the lips.

Additional ingredients include antioxidants, fats, fatty acid esters, protective agents, and other materials that are substantially free of water. For many embodiments, the formulation contains less than about 0.1 weight percent water. As discussed, the formulation of the present invention moisturizes lips for at least about 24 hours after application and for hours after lipstick color has worn off. The formulation moisturizes in a manner that enhances fullness of a user's lips when spheres trapped in the interstices of lip wrinkles swell as the spheres fill with transdermal water.

For some embodiments, the spheres are suspended in an oil such as castor oil and a liquid antioxidant such as tocopheryl acetate to make a sphere suspension. The antioxidant concentration ranges from about 0.5 to 2 percent by weight. The spheres range in concentration from about 0.01 to 1.5 weight percent. The spheres permit the formulation to expand in volume up to about 150% upon contact with moisture or water. A second mixture is prepared by mixing the sphere suspension with other ingredients of the formulation at a temperature within a range of about 30 to 50 degrees Centigrade.

The formulations of the present invention have use as lipstick, foundation, mascara, make-up, concealer, and so on.

One lipstick embodiment includes a wax in a concentration of 8–15 percent by weight, an oil in a concentration of 22–23 percent by weight; the spheres in a concentration of 4 to 12 percent by weight, an emollient in a concentration of 2–20 percent by weight, with the remaining components being other agents and adjutants.

The formulations of the present invention have a long lasting effect and a smoothing effect when applied to skin. The formulations do not bleed color and have an excellent skin compatibility. In a lipstick formulation, the spheres impart to lips a greater fullness than lips not treated with the lipstick display. The feel on the lips is pleasant and smooth. The lips appear to have a greater volume. One lipstick formulation is as follows:

EXAMPLE 1

Lipstick

| Component | wt % |
| --- | --- |
| Phase I | |
| Polyethylene | 7.7 |
| Ceresin Wax | 4.85 |
| Polyglyceryl-3 Beeswax | 6.17 |
| PVP/hexadecene | 2.5 |
| A Composition of 4 wt.% Lecithin, 12 wt. % C12–16 alcohols, 14 wt. % Stearic Acid, 16 wt. % Palmitic Acid, 27 wt. % Behenyl Alcohol, 27 wt. % Glyceryl Stearate | 2.0 |
| Sorbitan Sesquioleate | 1.5 |
| DL Tocopherol | 0.2 |
| Oleyl Alcohol | 7.5 |
| Propylparaben | 0.2 |
| Jojoba esters | 15.5 |
| Triisostearin | 8.0 |

| Component | wt % |
| --- | --- |
| Squalane | 4.0 |
| Isoeicosane | 2.0 |
| Ethylhexyl Palmitate | 4.48 |
| Phase 2 | |
| Titaniumdioxide blend of 40 wt. % Titanium Dioxide, 0.05 wt. % Tocopherol, 59.95 wt. % Ricinus Communis Seed Oil | 0.92 |
| CORed7SQ that includes 0.041 wt. % tocopherol, 33 wt. % CI 15850, 66.959 wt. % Ricinus Communis Seed Oil | 17.19 |
| COBlue1SO of 0.045 wt. % Tocopherol, 25 wt. % CI 42090, 74.955 wt. % Ricinus Communis Seed Oil | 0.56 |
| Mica of 23.500 wt. % CI 77891 and 76.500% mica | 1.12 |
| Silica of 5.000 wt. % methicone and 95.000 wt. % silica | 2.50 |
| Castor Oil of 0.0400 wt. % Tocopherol and 99.96 wt. % Ricinus Communis Seed Oil | 2.32 |
| Phase 3 | |
| Castor Oil of 0.0400 wt. % Tocopherol and 99.96 wt.% Ricinus Communis Seed Oil | 3.00 |
| Silk Mica | 2.19 |
| Phase 4 | |
| Sodium Polyaspartate (34.0 wt. %) and Aqua (66.0 wt. %) | 0.100 |
| Vegetal Fill Sphere of 0.0500 wt % butylparaben 0.0500 wt % ethylparaben 0.0500 wt % isobutylparaben 0.0500 wt % propylparaben 0.2300 wt. % methylparaben 0.3600 wt. % acacia senegal 0.5700 wt. % phenoxyethanol 1.0000 wt. % butylene glycol 1.6400 wt. % Aqua 3.0000 wt. % Silica Dimethyl Silylate 93.0000 wt. % Pentaerythrityl Tetraisostearate Phase 5 | 3.000 |
| Parfum | 0.5 |

The components of phase 1 were mixed in a container at about 85–95 degrees Centigrade. While holding the temperature at this level, the components of phase 2 were added and mixed until they were evenly distributed. After adding phase 3 at 80–85 degrees Centigrade, phase 4 was added to the mixture of phases 1–3, also at a temperature of about 70–75 degrees Centigrade. After mixing briefly for about 1 minute, phase 5 was added. The finished mixture was poured into lipstick molds and was cooled.

EXAMPLE 2
Lipstick

| Component | wt % |
| --- | --- |
| Phase 1 | |
| Carnauba Wax | 2 |
| Candilla Wax | 6.5 |
| Ozocerite | 3 |
| Behenyl Erucate | 2.5 |
| Myristyl Myristate | 3 |
| Oleyl alcohol | 11 |
| Lanolin | 8 |
| Polydecene | 9.5 |
| Ca-Al-B Silicate | 2.5 |
| Phase 2 | |
| Castor Oil | |
| Phase 3 | |
| Dyes | 8 |
| Castor Oil and Spheres and tocopherol | 11 |
| Phase 4 | |
| Mica | 2 |
| Phase 5 | |
| Spheres | 7 |
| Caster oil | 7 |
| Tocopherol acetate | 1 |
| Phase 6 | |
| Fragrance | 1 |

The components of phase 1 were mixed in a container at about 85–95 degrees Centigrade. While holding the temperature at this level, the components of phase 2 were added and mixed until they were evenly distributed. After adding phase 3 at 80–85 degrees Centigrade, phase 6 was added to the mixture of phases 1–4, also at a temperature of about 70–75 degrees Centigrade. After mixing briefly for about 1 minute, phase 6 was added. The finished mixture was poured into lipstick molds and was cooled.

One other lipstick formulation is as follows:

EXAMPLE 3
Lipstick

| Component | wt % |
| --- | --- |
| Carnauba Wax | 2.5 |
| Candelilla Wax | 3.5 |
| Ozocerite | 7 |
| Behenyl Erucate | 2 |
| Caprylic/Capric Triglyceride | 9 |
| Polydecene | 6.5 |
| Lauryl Lysine | 2.5 |
| Castor Oil | Add to 100 percent |
| Colors | 10.5 |
| Mica | 5 |
| Spheres | 5 |
| Tocopherol Acetate | 2 |
| Fragrance | 1 |

One cream formulation is as follows:

EXAMPLE 4
Cream Foundation

| Component | wt % |
| --- | --- |
| Carnauba Wax | 4.5 |
| Tridecyl Trimellitate | 11.5 |
| Spheres | 6 |
| Castor Oil | 6 |

-continued

| Component | wt % |
| --- | --- |
| Butylparaben | 0.06 |
| Cetyaryl Octanoate | add to 100% |
| Magnesium Stearate | 3 |
| Polymethyl Methacrylate | 10 |
| Corn Starch | 3 |
| Colors | 4.5 |
| Mica | 21 |
| Talc | 18 |
| Silica | 2 |

One mascara formulation is as follows:

EXAMPLE 5
Mascara

| Component | wt % |
| --- | --- |
| Stearic Acid | 9 |
| Montan Wax | 1.5 |
| Beeswax | 8.5 |
| Isopropyl Lanolate | 3.5 |
| Spheres | 4 |
| PVP/Eicosene Copolymer | 0.5 |
| Castor Oil | Add to 100% |
| Glycerin | 2 |
| Hectorite | 0.3 |
| Acacia Catechu | 2 |
| Colors | 13 |
| Mica | 2 |
| Trisamino | 2 |
| Diazolidinyl Urea | 0.3 |
| Phenoxyethanol | 1.0 |
| Fragrance | 0.3 |

A lipstick product of the present invention was tested in a population of seventy-five (75) female subjects, each of whom was at least about 30 years old. Each test subject had dry lips and exhibited some visible signs of vertical lines, dryness and chappiness on their lips. Each test subject participated in the test for 24 hours. Subjects visited a test center on test day and were instructed to apply a test lipstick on their lips immediately after the first baseline moisture measurement, hour 0. Moisture measurements were made by measuring electrical impedance on lips. All subjects again applied lipstick at 4 and 8 hours after the first application. Thereafter, lip moisturization measurements were obtained at twelve and twenty-four hours after the first treatment. Excess lipstick was removed before measurements.

Subjects using Retin-A, analogs, corticosteroids, benzoyl peroxide and topical antibiotics were excluded. Subjects that had facial peels or dermabrasion within the past year were also excluded. Subjects having psoriasis, eczema, or atopic dermatitis or any diseases associated with lips were excluded. Subjects in clinical studies for topical or systemic medications or products or subjects with known communicable diseases were excluded.

A five day dry out period preceded the study to ensure that all subjects were at a baseline value and to factor out differences in effects of current lip care regimens. On day 5, subjects visited the test center and were given a bar of soap to wash their entire facial area as well as their lips, as often as they chose. Subjects were not allowed to use any moisturizer, sunscreen, nor lip product during this phase of the study. The subjects were instructed to avoid excessive UV exposure, and were not allowed to visit tanning salons. Subjects were allowed to use eye and some face products, blush, during the study.

On test day, all subjects visited the test center with no product applied to their faces and lips. Subjects were given instructions on how to use the test products. Impedance measurements of lip hydration were made in each test subject before the first application and at 12 and 24 hours after the first application. Residual lipstick was removed before measurements.

Lip hydration performance was measured via impedance measurements on the central area of the lower lips of subjects. Measurements were taken in duplicate and were averaged. Results are presented in Tables 1a, 1b and 1c. The results indicate that averaged baseline impedance values of the subjects' lips were found to range from 90 to 108 which are indicative of a very dry condition of the lips. In accordance with protocol, subjects were asked to apply lipstick of the present invention immediately after baseline measurement and then to reapply at 4 and 8 hours after the first application.

Measurements were then taken at 12 and 24 hours after the first application. The impedance measurements for a lipstick formulation with 3% vegetal spheres complex by weight are shown in Table 1. The impedance measurements for a lipstick formulation with 1.5% vegetal sphere complex by weight are shown in Table 2. The impedance measurements for a lipstick formulation free of vegetal sphere complexes are shown in Table 3.

As the results indicate, all three lipsticks tested provided increases in lip moisturization to a varying degree at 12 hours. Comparatively, a lipstick formulation having 3% vegetal sphere complex by weight provided the greatest moisturization followed by a lipstick formulation with 1.5% vegetal sphere complex by weight and a lipstick formulation free of vegetal spheres, which was the least effective. At 24 hours after the first treatment, while lipstick free of vegetal sphere complex or having 1.5% spheres retained only small increases in lip moisturization over baseline values, the lipstick formulation containing 3% vegetal sphere complex by weight still displayed significant improvement in lip hydration. The results suggest that the lipstick containing 3% vegetal sphere complex was more effective and provided much longer lasting lip hydration than the other two lipsticks tested.

TABLE 1A

Lip Moisturization via Impedance Measurement
Moisture Lipstick:
(3% Vegetal Sphere Complex)

| Subject# | Hour 0 | Hour 12 | Hour 24 |
| --- | --- | --- | --- |
| 1 | 98 | 130 | 112 |
| 2 | 90 | 106 | 98 |
| 3 | 96 | 162 | 106 |
| 4 | 102 | 241 | 162 |
| 5 | 94 | 162 | 140 |
| 6 | 102 | 141 | 126 |
| 7 | 96 | 153 | 132 |
| 8 | 102 | 128 | 98 |
| 9 | 96 | 124 | 116 |
| 10 | 98 | 108 | 102 |
| 11 | 94 | 122 | 110 |
| 12 | 92 | 180 | 116 |
| 13 | 100 | 142 | 128 |
| 14 | 96 | 130 | 108 |
| 15 | 94 | 122 | 96 |
| 16 | 92 | 128 | 108 |
| 17 | 94 | 140 | 102 |
| 18 | 90 | 118 | 96 |
| 19 | 90 | 122 | 108 |
| 20 | 98 | 130 | 122 |

TABLE 1A-continued

Lip Moisturization via Impedance Measurement
Moisture Lipstick:
(3% Vegetal Sphere Complex)

| | | | |
|---|---|---|---|
| 21 | 96 | 122 | 120 |
| 22 | 92 | 140 | 126 |
| 23 | 92 | 130 | 102 |
| 24 | 96 | 128 | 116 |
| 25 | 90 | 124 | 108 |
| Average: | 95.20 | 137.32 | 114.32 |
| S.D. | 3.79 | 27.44 | 15.43 |
| t | | −7.998 | −6.748 |
| p* | | <0.0001 | <0.0001 |
| % Change | | 44.24% | 20.08% |

*Paired T Test at 95% confidence limited

TABLE 1B

Lip Moisturization via Impedance Measurement
Moisture Lipstick:
(1.5% Vegetal Sphere Complex)

| Subject# | Hour 0 | Hour 12 | Hour 24 |
|---|---|---|---|
| 1 | 100 | 138 | 102 |
| 2 | 102 | 108 | 96 |
| 3 | 92 | 126 | 102 |
| 4 | 104 | 142 | 108 |
| 5 | 106 | 128 | 100 |
| 6 | 108 | 130 | 100 |
| 7 | 92 | 104 | 92 |
| 8 | 96 | 104 | 96 |
| 9 | 92 | 102 | 94 |
| 10 | 94 | 98 | 92 |
| 11 | 92 | 142 | 110 |
| 12 | 96 | 110 | 96 |
| 13 | 92 | 122 | 102 |
| 14 | 100 | 112 | 102 |
| 15 | 96 | 122 | 98 |
| 16 | 94 | 108 | 94 |
| 17 | 94 | 116 | 100 |
| 18 | 92 | 125 | 106 |
| 19 | 92 | 162 | 120 |
| 20 | 90 | 120 | 106 |
| 21 | 90 | 102 | 94 |
| 22 | 92 | 106 | 108 |
| 23 | 94 | 124 | 102 |
| 24 | 96 | 148 | 110 |
| 25 | 100 | 168 | 98 |
| Average: | 95.84 | 122.68 | 101.12 |
| S.D. | 5.03 | 18.84 | 6.71 |
| t | | −7.390 | −3.042 |
| p* | | <0.0001 | 0.005 < p < 0.01 |
| % Change | | 20.01% | 5.51% |

*Paired T Test at 95% confidence limited

TABLE 1C

Lip Moisturization via Impedance Measurement
Moisture Lipstick:
(0% Vegetal Sphere Complex)

| Subject# | Hour 0 | Hour 12 | Hour 24 |
|---|---|---|---|
| 1 | 98 | 116 | 120 |
| 2 | 98 | 180 | 108 |
| 3 | 98 | 124 | 92 |
| 4 | 94 | 100 | 92 |
| 5 | 104 | 122 | 102 |
| 6 | 92 | 114 | 98 |
| 7 | 94 | 250 | 124 |
| 8 | 98 | 136 | 96 |
| 9 | 90 | 108 | 98 |

TABLE 1C-continued

Lip Moisturization via Impedance Measurement
Moisture Lipstick:
(0% Vegetal Sphere Complex)

| | | | |
|---|---|---|---|
| 10 | 92 | 142 | 110 |
| 11 | 90 | 102 | 106 |
| 12 | 90 | 110 | 112 |
| 13 | 96 | 116 | 102 |
| 14 | 98 | 98 | 94 |
| 15 | 92 | 120 | 108 |
| 16 | 94 | 118 | 110 |
| 17 | 94 | 114 | 94 |
| 18 | 102 | 122 | 96 |
| 19 | 100 | 146 | 108 |
| 20 | 102 | 130 | 102 |
| 21 | 98 | 108 | 106 |
| 22 | 92 | 116 | 98 |
| 23 | 90 | 132 | 98 |
| 24 | 94 | 104 | 100 |
| 25 | 92 | 128 | 100 |
| Average: | 95.28 | 126.24 | 102.72 |
| S.D. | 4.12 | 31.13 | 8.40 |
| t | | −4.995 | −3.882 |
| p* | | <0.0001 | 0.0005 < p > 0.001 |
| % Change | | 32.49% | 7.81% |

*Paired T Test at 95% confidence limited

Although this invention has been described with a certain degree of particularity with respect to certain ingredients, it is understood that the present disclosure has been made only by way of example and that numerous changes in the details of the composition may be resorted to without departing from the spirit and scope of the invention.

What is claimed is:

1. A cosmetic formulation comprising a plurality of spheres comprising vegetal protein, the spheres having a first desiccated volume and having a second hydrated volume, wherein the hydrated volume is at least about one hundred times greater than the desiccated volume.

2. The cosmetic formulation of claim 1 wherein the second hydrated volume of the spheres is several hundred times greater than the desiccated volume.

3. The cosmetic formulation of claim 1 wherein the formulation is a lipstick.

4. The cosmetic formulation of claim 3 wherein the spheres comprise a concentration of at least about 0.01 to 1.5 percent by weight of the lipstick formulation.

5. The cosmetic formulation of claim 1 further comprising an oil wherein the spheres are suspended in the oil.

6. The cosmetic formulation of claim 5 wherein the oil is castor oil.

7. The cosmetic formulation of claim 1 wherein the desiccated volume of the spheres is about 20 microns.

8. A method for decreasing wrinkles in lips and increasing lip fullness, comprising:

preparing a lipstick comprising a plurality of spheres comprising vegetal protein, the spheres having a first desiccated volume and having a second hydrated volume, wherein the hydrated volume is at least about one-hundred times greater than the desiccated volume; and applying the lipstick to lips so that the lipstick penetrates wrinkles and so that the spheres are hydrated by water in the lips thereby increasing the volume of the spheres and increasing lip fullness.

9. The method of claim 8 wherein the spheres have the desiccated volume prior to application to lips.

10. A method for making a lipstick, comprising:

providing a plurality of spheres comprising vegetal protein that have a desiccated volume and a hydrated volume wherein the hydrated volume is at least about 100 times greater than the desiccated volume;

suspending the plurality of spheres in an oil or a silicone; and adding coloring agents to the plurality of spheres in an oil.

11. The method of claim 10 further comprising providing a wax to the plurality of spheres in an oil or silicone.

12. The method of claim 10 further comprising adding one or more adjuvant selected from the group consisting of alcohols, polyols, stearic acid, magnesium stearate, cetearyl octanoate, corn starch, and organic light stabilizers.

13. The method of claim 10 further comprising adding an emollient.

14. The method of claim 10 further comprising adding a powder.

15. A lipstick comprising:

a phase comprising a wax, an alcohol, and lanolin;

a phase comprising castor oil;

a phase comprising a coloring agent, an oil, and a plurality of spheres comprising vegetal protein that have a desiccated volume and a hydrated volume wherein the hydrated volume is at least about 100 times greater than the desiccated volume;

a phase comprising mica;

a phase comprising the plurality of spheres and an oil and an antioxidant; and a phase comprising a fragrance.

16. A lipstick comprising:

a wax;

a triglyceride;

polydecene an oil;

a plurality of spheres comprising vegetal protein that have a desiccated volume and a hydrated volume wherein the hydrated volume is at least about 100 times greater than the desiccated volume;

a coloring agent; and an antioxidant.

17. A method for moisturizing lips for a period of time up to at least about 24 hours after application of a lipstick, comprising:

providing a lipstick comprising a plurality of spheres comprising vegetal protein that have a desiccated volume and a hydrated volume wherein the hydrated volume is at least about 100 times greater than the desiccated volume; and applying the lipstick to a user's lips.

18. The method of claim 17 wherein the lipstick is substantially free of moisturizers.

19. The method of claim 17 wherein lip moisturizing occurs after the lipstick has worn off a user's lips.

20. The method of claim 19 wherein the lipstick is substantially free of water.

21. A method for making a lipstick that moisturizes lips for at least about 24 hours after application of the lipstick to lips, comprising:

providing a plurality of spheres, the spheres comprising vegetal protein having a first desiccated volume and having a second hydrated volume, wherein the hydrated volume is at least about one hundred times greater than the desiccated volume; and blending the plurality of spheres, in a concentration of at least about 3 percent by weight, with material that is substantially free of water.

22. The method of claim 21 wherein the lipstick is substantially free of moisturizers.

* * * * *